United States Patent [19]

Katsuki et al.

[11] Patent Number: 4,471,130
[45] Date of Patent: Sep. 11, 1984

[54] METHOD FOR ASYMMETRIC EPOXIDATION

[75] Inventors: Tsutomu Katsuki, Sagaken, Japan; Karl B. Sharpless, Portola Valley, Calif.

[73] Assignee: The Board of Trustees of the Leland Stanford Junior University, Stanford, Calif.

[21] Appl. No.: 287,012

[22] Filed: Jul. 27, 1981

Related U.S. Application Data

[63] Continuation-in-part of Ser. No. 175,786, Aug. 6, 1980, abandoned.

[51] Int. Cl.$^3$ .............................................. C07C 45/04
[52] U.S. Cl. ................................. 549/523; 260/429 R; 260/429.5; 536/124; 536/127; 536/7.2; 560/218; 562/402; 562/401; 568/902; 568/913
[58] Field of Search ........................ 549/523; 536/124; 260/429.5, 429 R

[56] References Cited

U.S. PATENT DOCUMENTS 2,867,577  1/1959  Urban, Jr. et al. .................. 549/523
3,436,409  4/1969  Hill et al. ............................ 549/523
3,935,272  1/1976  Chapurlat ........................... 549/523

OTHER PUBLICATIONS

Yamada et al., "Jour. Amer. Chem. Soc.", vol. 99, Mar. 1977, pp. 1988–1990.
Michaelson et al., "Jour. Amer. Chem. Soc.", vol. 99, Mar. 1977, pp. 1990–1992.
Tani et al., "Tetrahedron Letters", vol. 32, pp. 3017–3020, 1979.

Primary Examiner—Johnnie R. Brown
Attorney, Agent, or Firm—Bertram I. Rowland

[57] ABSTRACT

Methods and compositions are provided for asymmetrically donating an oxygen atom to a pair of electrons to produce an asymmetric product. Specifically, a metal alkoxide is used as a catalyst, where the metal has a coordination number of at least four, and at least one, usually two, of the alkoxide groups bonded to the metal are bonded to asymmetric carbon atoms. The metal catalyst is employed in conjunction with a hydroperoxide and an alkanol having a functionality with a pair of electrons capable of accepting an oxygen atom. The resulting product is enriched in one enantiomer due to the enantioselective introduction of an asymmetric center or an enhanced rate of reaction of one of the enantiomers of a chiral alkanol.

12 Claims, No Drawings

METHOD FOR ASYMMETRIC EPOXIDATION

This invention was made at least in part in the course of a grant from the National Institutes of Health (GM24551).

This is a continuation-in-part of pending prior application Ser. No. 175,786 filed on Aug. 6, 1980, now abandoned, of Karl Sharpless and Tsutomu Katsuki for THE FIRST PRACTICAL METHOD FOR ASYMMETRIC EXPOXIDATION.

BACKGROUND OF THE INVENTION

1. Field of the Invention

The ability to introduce a chiral center stereospecifically or resolve a racemic mixture has broad industrial applications. Natural products having chiral centers are normally stereoisomeric, with only one of the stereoisomers being physiologically active. Where synthesizing or modifying a natural product involving the formation of a stereoisomeric center, the ability to introduce the functionality asymmetrically is of extreme economic importance. Where only one enantiometer is active, not only is half of a racemic product inactive, but where it is required to separate the inactive product, the recovery of the desired stereoisomer results in further losses of the desired product. In synthetic procedures involving a number of steps, an intermediate or final step resulting in a yield less than 50% will seriously affect the economics of the synthetic approach.

Furthermore, with polymers, stereoregularity can provide for greatly enhanced physical properties. Because asymmetric compounds other than naturally occurring compounds are frequently costly, stereoregular polymers of asymmetric monomers have not found extensive use.

There has been, therefore, a continuing interest in being able to prepare compounds by asymmetric induction to provide a product having enhanced amounts of a particular stereoisomer.

2. Description of the Prior Art

Methods of asymmetric synthesis may be found in J. D. Morrison and H. S. Mosher, "Asymmetric Organic Reactions," Prentice-Hall, Englewood Cliffs, N.J., 1971 258–62; S. Yamada et al. J. Am. Chem. Soc., 99, 1988 (1977); R. C. Michaelson et al. ibid., 99 1990 (1977); H. B. Kagen et al. Angew. Chem. Int. Ed. Eng., 18 45 (1979) K. Tani et al., Tetrahedron Lett., 3017 (1979); and H. Wynberg and B. Marsman, J. Org. Chem., 45 158 (1980); K. B. Sharpless and T. R. Verhoeven, Aldrichimica Acta, 12 63 (1979). Tani et al., Tetra. Letters 32, 3017–3020 (1979) describe the use of molybdenum catalysts to symmetrically epoxidize olefinic hydrocarbons in the presence of chiral diols.

SUMMARY OF THE INVENTION

Methods and compositions are provided for asymmetric transfer of oxygen from a hydroperoxide to a functionality having a pair of electrons capable of accepting an oxygen atom to form a covalent bond to provide oxides (includes epoxides) and for kinetic resolution to high optical purity. The method employs a metal alkoxide catalyst where the metal has a coordination number of at least four, and at least one of the alkoxides bonded to the metal is asymmetric. The catalyst, substrate and hydroperoxide are combined in an inert medium under mild conditions for a time sufficient to oxidize the substrate and the asymmetrically oxidized product and/or unreacted starting material isolated or further transformed as desired.

DESCRIPTION OF THE SPECIFIC EMBODIMENTS

Method and compositions are provided for asymmetric induction involving transfer of an oxygen atom from a peroxide to a functionality in an alkanol having a pair of electrons capable of accepting the oxygen atom to form a bond, usually stable. The primary constituents of the method are the metal catalyst having an asymmetric alkoxide as a ligand; the alkanol, and the peroxide. In discussing the subject invention, the components indicated above will first be described, followed by a description of the method, setting forth any other components and conditions employed in the method.

COMPOSITIONS

Catalysts

The catalysts employed in the subject method involve metal alkoxides, where the metal has a coordination number of at least four, usually six, and wherein at least one of the alkoxides bonded to the metal is asymmetric.

The metal will be a metal of Groups 4b to 6b of atomic number 22 to 74, particularly those metals of groups 4b to 5b of atomic number 22 to 73 of the Periodic Chart. (Handbook of Chemistry and Physics, 44th ed. Chemical Rubber Publishing Co., pp. 448–9). The metals of interest include titanium, tantalum, zirconium, hafnium, niobium, vanadium, and molybdenum, particularly the first four metals indicated and more particularly titanium and tantalum.

The asymmetric alkoxide can be a monool or a diol, particularly a vicinal diol or 1,3-diol. That is, the hydroxyl groups will be separated by from two to three carbon atoms. Normally, in the diols, both of the hydroxyls will be enantiomeric and usually of the same configuration, rather than opposite configuration. That is, both of the chiral centers will be R or S, rather than one being R and the other being S. The asymmetric alkoxide may be water soluble or insoluble.

The remaining portion of the asymmetric alkoxide molecule, particularly of the glycol, may be hydrocarbon, which includes aliphatic particularly alkyl, alicyclic, aromatic, or combinations thereof; substituted hydrocarbon, where the substituent can be of a wide variety of groups, since the substituent will normally not play a critical role in the reaction, but must not be a reactive group which interferes with the role of the catalyst, so that any inert (unreactive) substituent may be employed; or a functionality, which is unreactive, and desirably has an oxygen and/or neutral nitrogen bonded to carbon. The significant factor in all of the substituents is that the functionalities present, if any, must not react with the reactants in the medium to interfere with the transfer of the oxygen atom, nor to provide a product which results in the formation of water.

The chiral alkanols (including glycols) will be monomeric or polymeric, when monomeric will be of at least three carbon atoms, usually at least four carbon atoms, having one or more alkanolic hydroxyl groups, usually not more than three hydroxyl groups, preferably two hydroxyl groups, which are separated by two to three carbon atoms and will generally have not more than about 30 carbon atoms, more usually not more than about 20 carbon atoms, and most usually not more than about 10 carbon atoms. The number of heteroatoms other than the oxygens of the hydroxyls will be from 0 to 12 more usually from 0 to 10, preferably from 2 to 10, and more preferably from 2 to 6. The heteroatoms will for the most part be chalcogen, nitrogen and halogen.

Functionalities will include oxygen as oxo:oxocarbonyl, and non-oxo-carbonyl; and oxy bonded solely to carbon and such other functionalities which will be described subsequently; sulfur, bonded solely to carbon, nitrogen and chalcogen (sulfur and oxygen), which sulfur when present as thioether, under the conditions of the reaction, will normally be oxidized to sulfoxide or sulfone, which groups are also included, sulfonate ester and sulfonamide; nitrogen, normally as non-basic amino, particularly tertiary, or amide; halogen, normally as aryl halogen, usually of atomic number 9 to 17. The chiral alkoxide is desirably free of ethylenic unsaturation, since under the conditions of the reaction such ethylenic bonds could be oxidized. Preferably the chiral alkoxide will be a secondary alkoxide.

As for other heterofunctionalities, except for those alpha to the carbinol group, since they will normally not participate in the reaction, they will only be chosen where they provide some advantage in isolation, solubility, or the like.

The polymeric chiral carbinol can be an addition or condensation polymer having side chains coming within the monomeric chiral alkanol definition.

The number of chiral carbinols bonded to the metal will be at least one, normally two and may be more, although optimum results are obtained with two chiral centers bonded to the metal. The catalyst may have from one to two metal atoms in a molecule.

The non-chiral alkoxides bonded to the metal may be any hydroxyl functionality free of interfering groups, but will conveniently be aliphatic alcohols, generally of from 1 to 12, more usually of from 1 to 6 carbon atoms. Preferably, the alkoxides will be relatively bulky, having from 3 to 6 carbon atoms, preferably being branched at the alpha carbon atom, normally one to two branches. Particularly preferred is isopropoxide and tert.-butoxide. It should be clearly understood, that the alkanols are solely chosen for convenience and any carbinol may be employed, so long as the substituents on the carbinol do not interfere with the course of the reaction. As to all of the components of the reaction mixture, acidic groups e.g. carboxylic and sulfonic acids, and basic amino groups should be avoided. Illustrative alkoxides include methoxide, ethoxide, propoxide, isopropoxide, butoxide, tert.-butoxide, hexoxide, and the like.

The preparation of the catalyst is conventional and can be performed in situ. The alkoxide substituted dihalo metal may be combined with the chiral alkoxide of an appropriate metal e.g. lithium or sodium, in an inert polar solvent, and the product separated from the inorganic salt. More conveniently, the polyalkoxide of the metal may be combined with the chiral alkoxide in approximately stoichiometric amounts in an inert solvent. There is no requirement that the alcohol which is formed be removed.

Compounds which are illustrative of the chiral carbinols are as follows:

TABLE I 1,2-propylene glycol
2,3-butanediol
3,4,-dimethyl-3,4-hexanediol
4,5-octandiol
2,3,-hexandiol
1,3-di(p-nitrophenyl)propan-1,2-diol
2,4-pentanediol
dimethyl tartrate
diisopropyl tartrate
distearyl tartrate
diphenyl tartrate
tartaric acid diamide
N,N-dimethyl tartaric acid diamide
trans-1,2-cyclopentandiol
diethyl 1,2-cyclohexandiol-1,2-dicarboxylate
dimethyl 2,4-dihydroxyglutarate
ethyl N,N-diethyl tartrate monoamide
2,5-dioxo-3,4-octandiol
1,2-bis-acetylethylene glycol
bis-2,2'-(2-hydroxycaprolactone)

Of particular interest as catalyst are compounds combining di(alpha-oxo substituted) vicinal glycols in combination with titanium, where the ratio is one glycol and two alkoxides per titanium. For the most part, the catalyst will have the following unit formula:

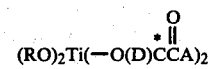

wherein:

R is a non-interfering group, conveniently alkyl of from 1 to 8 carbon atoms, usually of from 1 to 6 carbon atoms, more usually of from 2 to 4 carbon atoms and particularly as described previously for the non-chiral carbinol;

the two Ds are the same or different and are hydrogen, alkyl of from 1 to 6, more usually 1 to 4, preferably 1 to 2 carbon atoms or two Ds may be taken together to form a ring with the carbons to which they are attached of from 4 to 8, usually from 5 to 6 carbon atoms, preferably hydrogen;

* intends an asymmetric carbon bonded to the other asymmetric carbon to define a vicinal glycol.

A is saturated hydrocarbyloxy of from 1 to 12, more usually of from 1 to 6, preferably of from 1 to 4 carbon atoms, usually aliphatic and free of aliphatic unsaturation, hydrocarbyl of from 1 to 12, usually of from 1 to 6, more usually of from 1 to 4 carbon atoms, particularly alkyl, amino, alkylamino and dialkylamino, where each of the alkyl groups is of from 1 to 6, more usually of 1 to 4 carbon atoms, or the two As may be taken together to form a carbocyclic ring of from 5 to 7 carbon atoms; the two As may be the same or different and where one of the As is amino, it is preferred that the As be different.

Based on evidence of the results with the use of mixtures of chiral alkoxides with titanium it is believed that the catalyst is oligomeric, particularly dimeric. The dimeric catalyst will for the most part have the following formula:

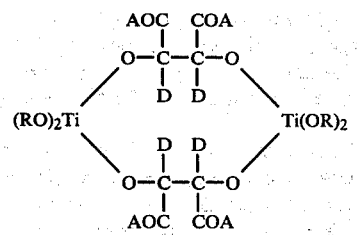

where the symbols have all been defined previously.

Substrate

The substrate employed for the above described catalyst is characterized by having a carbinol group, which may or may not be asymmetric, being chiral or prochiral, and a functionality having a pair of electrons which is capable of accepting an oxygen atom to form a covalent bond. The chirality may be at the carbinol or at some other site in the molecule, usually not too remote from the carbinol preferably within about ten atoms. The oxygen accepting functionality will be separated from the carbinol carbon by from 0 to 2, usually 0 to 1 carbon atoms. Where the functionality is an aliphatically unsaturated group i.e. a double or triple bond, the multiple bond will normally be separated by from 0 to 2 atoms, usually 0 to 1 atom, preferably being bonded to the carbinol carbon. Where the functionality is other than the multiple bond, the functionality will normally be separated from the carbinol by from 1 to 3 atoms. The separating atoms are normally carbon atoms.

The atom separation indicated is directed to a spatial relationship between the hydroxyl of the carbinol and the oxygen accepting functionality. There will be instances where the hydroxyl of the carbinol and the oxygen accepting functionality will be separated by many more atoms than specified above, but within the spatial requirements for asymmetric transfer of oxygen to the oxygen accepting functionality, the unbonded distance will fulfill the spatial requirement. Because these compounds will be a relatively narrow class of compounds and normally have special constraints, there is no simple way to describe them, but it should be understood that they could be employed in the subject invention, although outside the literal limitations indicated above.

Substrates will be employed for two purposes. The first purpose will be enantioselective epoxidation. Usually, with a chiral carbinol, one enantiomer of the erythro diasteriomer results. The second purpose will be to resolve a racemic mixture of a chiral carbinol by preferential oxidation of one of the enantiomers to provide optically active product and optically active starting material of the opposite configuration.

The functionalities which may be present for the oxidation to produce the enantiomer will normally be nitrogen or third row elements of atomic number 15 to 16, which elements are capable of accepting an oxygen atom to form a stable covalent bond. For the most part, these elements will be phosphorus and sulfur. These atoms should be free of functionalities which would react adversely either with catalyst or the hydroperoxide. That is, the atoms should be free of readily oxidizable hydrogen and carbon bonds. Particular, sulfur is the preferred functionality i.e. thioether.

Usually the oxygen accepting atom will be bonded solely to carbon, nitrogen and oxygen.

The substrates may be of from 3 to any number of carbon atoms since monomers, oligomers and polymers may be employed. Where monomeric compounds are involved, the monomers will be from about 3 to 60 carbon atoms, more usually from about 3 to 50 carbon atoms, and generally from about 4 to 40 carbon atoms. Higher yields are frequently obtained where the product is water insoluble, that is, having a solubility of less than about 1 gram per 100 ml at 20° C. Therefore, when feasible, where small molecules are involved as a substrate, to enhance the yield, the compound may be modified to reduce its water solubility. This can be achieved by introducing a removable functionality at a site remote from the oxidizable functionality.

The allylic groups may be mono-, di-, tri-, or tetrasubstituted with aliphatic, alicyclic or aromatic groups, particularly aliphatic and alicyclic groups, and the olefin may be exocyclic or endocyclic. The olefin should be allylic, homoallylic or bishomoallylic, particularly allylic. The propargyl group may be mono- or disubstituted.

Where a heteroatom is involved, it will be desirable that the heteroatom be bonded stably by non-oxidizable bonds to its substituents. For example, phosphorus should be present as phosphite or phosphinite, sulfur would be bonded to carbon and from zero to one oxygen or nitrogen. Nitrogen will normally be amino and bonded solely to carbon. The functionality may therefore be bonded directly to carbon or bonded through an oxygen to carbon.

For the most part, the substrates will have the following partial formula:

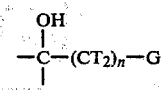

wherein:

where one of the atoms bonded to the carbinol carbon will usually be hydrogen, n is 0 to 3 being 0 to 2 when G is an olefin and 1 to 3 when G is other than an olefin;

T can be any inert group, free of active functionalities such as basic amines and acidic groups; and G is a group having a functionality having a pair of electrons capable of accepting an oxygen atom to form a bond and will normally be of at least one carbon atom and may be 60 carbon atoms or more, more usually not more than about 30 carbon atoms and has as the group having an oxygen accepting pair of electrons, a functionality such as alkene, alkyne, or a heterofunctionality having phosphorus or sulfur.

In view of the enormous diversity of carbinols, which may be employed as substrates, only various classes of products of interest can be suggested as useful in the subject process, either for synthesis of the particular product or for modification of an existing product, particularly a natural product.

The subject invention can be used in organic syntheses of enantiomers both for introduction of a variety of functionalities in a synthetic procedure and optical resolution of an enantiomer from a racemic mixture. The sole requirements for use of the subject invention in syntheses and/or resolution are the presence of (1) an hydroxyl group; (2) normally a chiral or prochiral center, which may or may not involve the hydroxyl, and (3) a functionality capable of accepting an oxygen atom to form a covalent bond, particularly aliphatic unsaturation, more particularly, ethylenic unsaturation.

General classes of compounds of interest include steroids, lipids, prostaglandins, terpenoids, hormones, saccharides, CNS drugs, α- and β-andrenergic blocking agents, antiarrythmic drugs, vasodilator drugs, analgesics, antibiotics, amino acids, and the like.

Illustrative compounds of interest for applying the subject invention in their synthesis and/or resolution include the acetonide of 2-methyl-1,3,4-trihydroxybutane, propanolol, 4-amino-3-hydroxybutyric acid, bestatin, α-methyldopa, propoxyphene, sphingosine, muscarine, ipsdienol, frontalin, acosamine, daunosamine, 4-deoxydaunosamine, ristosamine, vancosamine, epivancosamine, sibrosamine, gulono-1,4-lactone, cerulenin, spectinomycin, erythromycin, N-acetyl galactosamine, N-acetyl muramic acid, N-acetyl neuraminic acid, perillyl alcohol, methyl tetradeca-2,4,5-trienoate, disparlure, etc.

The following are a few synthetic procedures illustrating preparation of compounds employing the subject invention. Where the reagents involved are conventional, they are frequently omitted. The step(s) involving the subject invention is indicated by an asterisk.

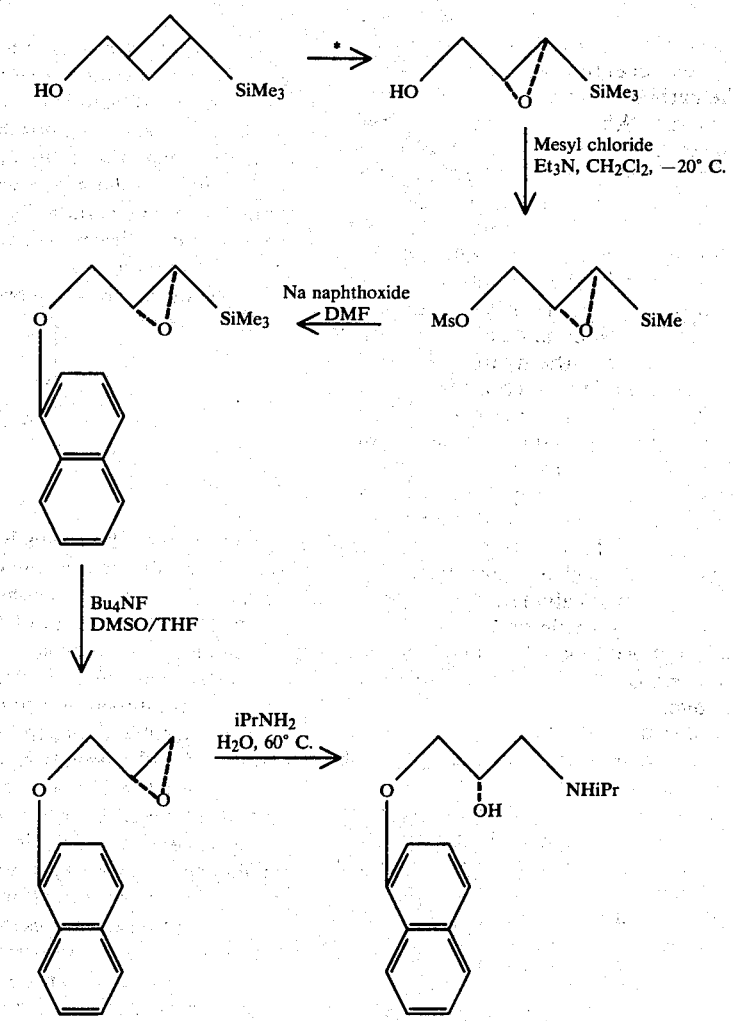

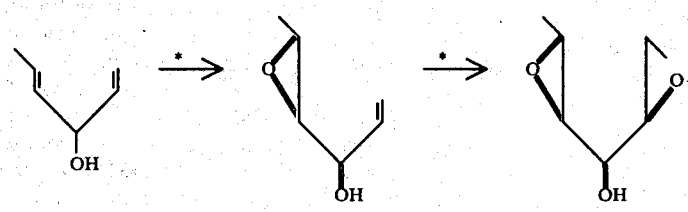

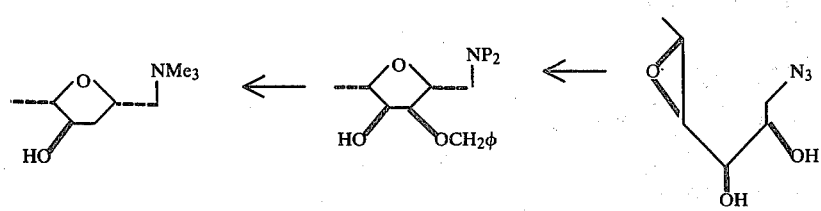
Preparation of Frontalin
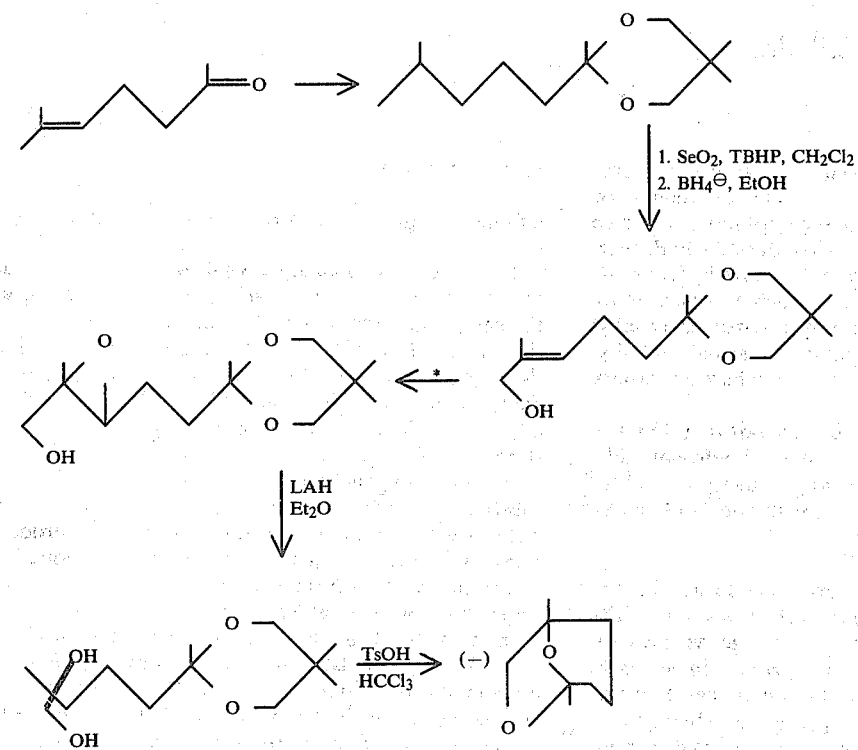
Preparation of bestatin
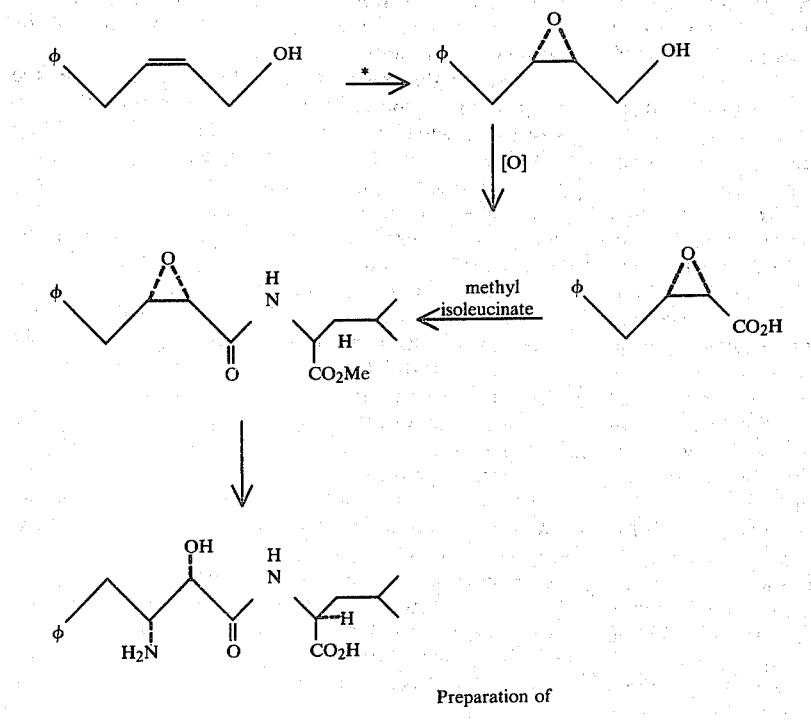
Preparation of -continued
4-amino-3-hydroxybutyric acid

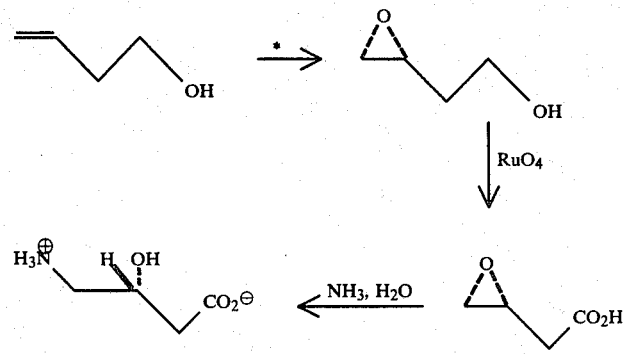

Hydroperoxide

The hydroperoxides will usually be aliphatic hydroperoxides. The hydroperoxides may be mono- or polyhydroperoxides, usually having not more than two hydroperoxide groups. For the most part, the hydroperoxides will be monohydroperoxides. The hydroperoxides will be from about 1 to 20 carbon atoms, more usually from 1 to 12 carbon atoms, particularly alkyl hydroperoxides having acceptable thermal stability, which for the most part will be secondary or tertiary hydroperoxides.

Illustrative hydroperoxides include tert.-butyl hydroperoxide, alpha, alpha-dimethylheptylhydroperoxide, bis-diisobutyl-2,5-dihydroperoxide, 1-methylcyclohexylhydroperoxide, cumene hydroperoxide, and cyclohexyl hydroperoxide.

Method

As the reaction medium, inert solvents will be employed, particularly halohydrocarbon solvents. The solvent should be relatively free of reactive protons, (particularly acidic) such as are present in alcohols, mercaptans, acids, or the like, but ethers can find use. The solvent should also be anhydrous, care being taken to remove substantially all of water to avoid catalyst hydrolysis.

Mild conditions will normally be employed, with temperatures below about 80° C., usually below about 30° C., and generally in the range of about −100° to 20° C., more usually in the range of about −50° to 10° C. The reaction is preferably carried out under an inert atmosphere, conveniently nitrogen.

The catalyst can be preprepared or conveniently prepared in situ. In preparing the catalyst, the metal alkoxide may be combined with the chiral alcohol, in a dry inert solvent at a temperature below 30° C. and in about stoichiometric proportions, although small excesses, generally less than about 50 mol % of the chiral carbinol may be employed. The reaction is then allowed to proceed for a sufficient time for the catalyst to form.

The catalyst can be preprepared by combining the metal alkoxide e.g. titanium tetralkoxide, the chiral alcohol e.g. tartrate ester, amide or half-ester amide, in at least stoichiometric proportions, generally not more than 50 mol % excess of the chiral alcohol, in an inert solvent and distilling off the alcohol from the alkoxide to drive the reaction to completion and remove the alcohol which appears to have an adverse effect.

Usually, the reaction forming the catalyst is complete in less than 30 min, more usually less than about 15 min. This will depend to some degree on the size of the reaction mixture, the concentrations employed, as well as the particular reactants. The time is not critical and will be optimized for a particular set of conditions and materials.

The amount of catalyst which is prepared in relation to the substrate may be varied widely, depending upon the nature of the substrate, the rate of reaction desired, the conditions under which the reaction is carried out, the concentrations employed, and the economics. Normally, there will be from about 0.001 to 1.5, more usually about 0.01 to 1 mole of catalyst per mole of substrate.

After a sufficient time for the catalyst to form, the substrate is added, while maintaining the temperature. After the addition of the substrate, the hydroperoxide is normally added in at least stoichiometric amount, and preferably in significant excess, usually at least 25% excess, more usually at least 50% excess, and not more than about 500% excess, usually not more than about 300% excess. That is, about 1 to 3 equivalents, preferably about 2 to 3 equivalents of the hydroperoxide will be used per equivalent of functionality to be oxidized.

The concentrations of the various materials may be varied widely, the catalyst normally being from about 0.005 to about 2M, preferably being from about 0.05 to 1M. The concentrations of the other reactions will be related accordingly.

After all the reactants have been combined in the inert medium, the reaction is continued until the substrate has been transformed to the desired degree. For a kinetic resolution, this may vary depending on whether the product or reactant is desired. The rate of the reaction varies depending upon the conditions and the amount of material involved, and may vary from a few minutes to a few days.

After completion of the reaction, the catalyst is destroyed using a mildly acidic aqueous solution, and where the oxidized substrate is in the organic layer, the organic layer isolated, dried and the product isolated. For water soluble products, salting out, extraction or chromatography may be required. Purification of the product may then be carried out in accordance with conventional means.

For water soluble substrates, conveniently an inorganic salt saturated aqueous solution e.g. saturated aqueous sodium sulfate, is added at a ratio of about 1 ml per mmole of substrate to the mixture, to effect destruction of the catalyst, in combination with a polar organic solvent e.g. diethyl ether, tetrahydrofuran, acetonitrile, etc., in about 1-2 ml per mmole of substrate. Temperature will generally range from about 0° C. to ambient.

After filtration, the organic solvent can then be dried and the product isolated.

The following examples are offered by way of illustration and not by way of limitation.

EXPERIMENTAL

A typical procedure is provided with comments (as appropriate) indicating the function of the particular condition, so that with other reactants, conditions can be varied accordingly.

A 500 ml, 1-necked round-bottomed flask equipped with a Teflon-coated magnetic stirring bar was oven-dried, then fitted with a serum cap and flushed with nitrogen. The flask was charged with 200 ml of dry (distilled from $CaH_2$) reagent grade dichloromethane and cooled by stirring in a $-23°$ C. bath (dry-ice/$CCl_4$).[a] Then the following liquids were added sequentially via syringe while stirring in the cooling bath: 5.94 ml (5.68 g, 20 mmol) titanium tetraisopropoxide (Aldrich); 3.43 ml (4.12 g, 20 mmol)[b] L(+)-diethyltartrate stirred five minutes before next addition; 3.47 ml (3.08 g, 20 mmol) of geraniol; and, finally, ca. 11 ml of dichloromethane solution (3.67M in TBHP) containing ca. 40 mmol (2 equiv) of anhydrous tert-butyl hydroperoxide (TBHP). [One can just as well use dichloroethane, carbon tetrachloride or hexane solutions of anhydrous TBHP. Complete experimental details for preparing these anhydrous TBHP solutions are given in Sharpless and Verhoeven supra.]

The resulting homogeneous solution was then stored overnight (ca. 18 hrs) in the freezer at ca. $-20°$ C. in the sealed (serum cap) reaction vessel [The progress of the epoxidation can be monitored by TLC]. Then the flask was placed in a $-23°$ C. bath (dry ice/$CCl_4$) and 50 ml of 10% aqueous tartaric acid solution was added while stirring; the aqueous layer solidified. After 30 minutes the cooling bath was removed and stirring was continued at room temperature for 1 hr or until the aqueous layer became clear. After separation of the aqueous layer, the organic layer was washed once with water, dried ($Na_2SO_4$), and concentrated to afford a colorless oil with an odor revealing contamination by TBHP.

This oil was diluted with 150 ml of ether and the resulting solution was cooled in an ice-bath, then 60 ml of 1N sodium hydroxide solution was added. This produced a two-phase mixture which was stirred at 0° C. for ½ hr.[c] The ether phase was washed with brine, dried ($Na_2SO_4$) and concentrated to give 4.24 g of a clear oil. Chromatography on silica gel afforded 2.6 g (77%) of 2(S),3(S)-epoxygeraniol, $[\alpha]^{24}_D - 6.36°$ (cl.5, $CHCl_3$). Analysis of this material as the MTPA ester[d] gave an enantiomeric excess of >95%. Whereas, analysis of the derived epoxyacetate using $Eu(hfbc)_3$ chiral shift reagent gave 94% e.e.

(a) Cooling serves two purposes. The obvious one of optimizing enantioselectivity, and the less obvious one of minimizing transesterification processes. Titanium alkoxides are excellent transesterification catalysts, and there is an extensive patent literature on this subject. We have now found that the rate of transesterification is substantially accelerated by an α-hydroxy substituent. Thus, in the presence of $Ti(OiPr)_4$ methyl mandelate transesterifies much faster than methyl phenylacetate. As α-hydroxy esters, the tartrates also undergo rather facile transesterification in our reaction system at room temperature. This produces tartrate esters which incorporate i-propanol and also the allylic alcohol substrate, and can give rise to problems at the product isolation stage. Fortunately, transesterification is slow at $-20°$ and running the reactions near that temperature has so far proved a viable solution to the problem.

(b) It is important to have at least one mole of tartrate per mole of $Ti(OR)_4$. Excess tartrate does not seem to matter, so a small excess (10 to 20 mole %) is added. In kinetic resolutions an excess of 20 mole percent or more is commonly added.

(c) Do not expose the reaction mixture to this base treatment for longer than ½ hr as base-catalyzed rearrangements of the epoxyalcohol may occur [G. B. Payne, J. Org. Chem., 27, 3819 (1962)]. Alternatively 1N NaOH in saturated brine may be employed. Diethyl tartrate is fairly soluble in water and hydrolyzes readily under these conditions. We have found that (+)-dimethyl tartrate (Aldrich) is as effective (>95% e.e.) as the ethyl ester for epoxidation of 4a. The methyl ester is much more water soluble and may prove advantageous when the hydrolysis step is unacceptable. The i-propyl ester also works well and is the tartrate of choice for kinetic resolutions.

(d) J. A. Dale, D. L. Dull, and H. S. Mosher, J. Org. Chem., 34, 2543 (1969). We used MTPA-chloride and DMAP in $CH_2Cl_2$.

TABLE II

Asymmetric Epoxidation of Allylic Alcohols

| Allylic Alcohol | Epoxyalcohol | % Yield[b] | % e.e[c] | Configuration[d] |
|---|---|---|---|---|
| Ia | Ib[e] | 77 | 95 (Eu,M) | 2(S), 3(S) |
| 2a | 2b[f] | 79 | 94 (Eu,M) | 2(S), 3(R) |

TABLE II-continued

| Substrate | Product | Yield | % ee | Config |
|---|---|---|---|---|
| 3a (OAc-geranyl type) | 3b | 70[g] | >95 (Eu) | 6(S), 7(S) |
| 4a[h] | 4b[i] | 87 | >95 (Eu) | 2(S), 3(S) |
| 5a | 5b[j] | 79 | >95 (M) | 2(S), 3(S) |
| 6a[k] | 6b[l] | 82 | 90 (M) | 2(S), 3(R) |
| 6a[k,m] | 6c | 80 | 90 (M) | 2(R), 3(S) |
| 7a[n] | 7b | 81 | >95 (M) | 2(S)[o] |
| 8a[p] | | 38 | 64 | 3(R) |

[a] Unless otherwise noted, all reactions were performed as described in detail for geraniol (1a). In most cases the scale was smaller (ca. 2 mmol).
[b] Isolated yields. All new compounds gave appropriate analytical and spectral data.
[c] The enantiomeric excesses were determined by $^1$H NMR on the corresponding epoxyacetates (pyridines/Ac$_2$O) in the presence of Eu(hfbc)$_3$ and/or by conversion to the MTPA ester followed by $^1$H or $^{19}$F NMR analysis. The technique(s) used is inidicated in parentheses. When both methods were employed, the % e.e. reported was an average of the two values.
[d] All absolute configurations were proven by chemical correlation as indicated for each case. All of the epoxyalcohols in the Table gave a negative rotation in CHCl$_3$ except for 4b and 6c.
[e] The enantiomer of 1b has been correlated with (R)—(−)-linalool.[1b]
[f] The enantiomer of 2b has been correlated with (S)—(+)-linalool.[1b]
[g] Alkaline hydrolysis step was omitted in this case; the diethyl tartrate was removed by chromatography. 6(S),7(S)—(−)-3b was correlated with (S)—(−)-6,7-epoxygeraniol [S. Yamada, N. Oh-hashi and K. Achiwa, Tetrahedron Lett., 2557 (1976)]. The 8-hydroxyl group of 3b was replaced by hydrogen via the following reaction sequence: TsCl/pyridine; NaI/acetone; NaH$_3$BCN/HMPA; LiOH/CH$_3$OH, H$_2$O.
[h] Epoxidation was performed at 0° C. and was completed in less than 30 min.
[i] 4b was correlated with methyl-(S)—(+)-2,3-diphenyl-2-hydroxypropionate (ii) [H. R. Sullivan, J. R. Beck and A. Pohland, J. Org. Chem., 28, 2381 (1963); see also E. Bye, Acta Chem. Scand., 27, 3403 (1973)]. Epoxyalcohol 4b was transformed to i by the following steps: RuO$_4$/CCl$_4$, CH$_3$CN, H$_2$O; CH$_2$N$_2$Et$_2$O; W-2 Raney nickel, H$_2$/absolute EtOH.
[j] 5b was correlated with (R)—(−)-tridecan-3-ol [K. Freudenberg, Stereochemie. Eine Zusammenfassung der Ergebnisse, Grundlagen und Probleme, p. 696, Ed. Franz Deuticke, Leipzig und Wien] by the following sequence: TsCl/pyridine; NaI/acetone; Zn/HOAc; H$_2$PtO$_2$.
[k] These results were obtained during enantioselective syntheses of both natural-(+)- and unnatural-(−)-disparlure.
[l] 6b was was correlated with unnatural-(−)-disparture.

TABLE II-continued

[m]In this case D-(−)-diethyl tartrate (the unnatural enentiomer) was used.
6c was correlated with natural-(+)-disparlure.
[n]This epoxidation was run for 40 hrs at −20° C. and a trace of 7a still remained.
[o]7b was correlated with (R)—(−)-2-cyclohexyl-2-butanol [D. J. Cram and J. Tadanier, J. Am. Chem. Soc., 81, 2737 (1959)] through the following steps:
LiAlH$_4$/Et$_2$O; TsCl/pyridine; LiCuMe$_2$/Et$_2$O.
[p]The alcohol is homoallylic and water soluble. Therefore the workup employed the saturated sodium sulfate-organic solvent combination.

Some additional commentary is worthwhile concerning the reaction procedure. Water soluble compounds are only difficultly isolated so that the technique described previously should be employed.

While the exemplary preparation described above employed a 1:1 molar ratio of catalyst to substrate, substantially smaller amounts may be employed with reactive allylic alcohols, for examples 1a, 2a, 3a, and 4a in Table II, where 0.1 equivalent of both titanium isopropoxide and diethyltartrate suffice. Under these conditions, the yields of 1b, 2b and 4b were comparable to or somewhat better than those with one equivalent of the catalytic materials and product isolations were cleaner and easier. However, the enantiomeric excess was somewhat poorer for 1b (91%) e.e. and 2b (84%) e.e. but was still greater than 95% e.e. for 4b. For less reactive substrates, 5a, 6a, and 7a of Table II, in order to obtain reasonable rates under the above conditions, the one equivalent was desirable. In employing the one equivalent with 7a, almost two days were required for completion.

The following study was made with a variety of chiral carbinols using the following procedure. A 0.5–1 mmol scale was employed. Freshly distilled anhydrous dichloromethane (10 ml) was cooled under nitrogen in an ice/salt bath and one eq. titanium isopropoxide added, followed by the addition of the chiral carbinol. After stirring for 5 min, 1 eq. of alpha-phenylcinnamyl alcohol (Table II, 4a) was added and after a 10 min interval, 2 eq. of t-butylhydroperoxide (solution in dichloromethane) was added. The progress of the reaction was monitored by tlc. At completion, 5 ml of a 10% tartaric acid solution was added and the mixture stirred until hydrolysis was complete as indicated by the appearance of two clear layers. The organic phase was separated, dried over magnesium sulphate and concentrated. The crude product was acetylated with acetic anhydride/pyridine and the acetate purified by tlc. Chiral shift studies were done in CDCl$_3$ at 60 MHz using Eu(hfbc)$_3$. Optical yields were confirmed by rotation. The following table indicates the results.

TABLE III

Chiral Carbinol (CC)

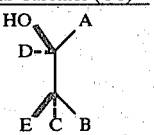

| A | B | C | D | E | e.e. %, Config. | CC/Ti mole Ratio |
|---|---|---|---|---|---|---|
| Me | Me | OH | H | H | 40,2S | 1:1 |
| φ | φ | OH | H | H | 0 | 1:1 |

TABLE III-continued

Chiral Carbinol (CC)

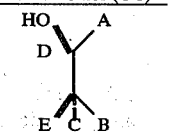

| A | B | C | D | E | e.e. %, Config. | CC/Ti mole Ratio |
|---|---|---|---|---|---|---|
| CO$_2$H | CO$_2$H | OH | H | H | 8,2S | 1:1 |
| CO$_2$C$_3$H$_6$OEt | CO$_2$C$_3$H$_6$OEt | OH | H | H | 93,2S | 1:1 |
| CO$_2$Et | CO$_2$Et | OH | Me | Me | 13,2S | 1:1 |
| CO$_2$Et | H | H | H | H | 10,2S | 2:1 |
| CO$_2$Et | CO$_2$Et | H | H | H | 0 | 1:1 |
| CO$_2$Et | H | OH | H | H | 65,2S | 1:1 |
| CH$_2$Pφ$_2$ (O=) | CH$_2$Pφ$_2$ (O=) | OH | H | H | 0 | |
| CONEt$_2$ | CONEt$_2$ | OH | H | H | 15,2R | 1:1 |
| CONH$_2$ | CONH$_2$ | OH | H | H | 15,2R | 1:1 |
| CO$_2$Et | CONHCH$_2$φ | OH | H | H | 60–80, 2R | 1:1 |
| —CO—N—CO— (CH$_2$φ) | | OH | H | H | 15,2S | 2:1 |
| CO$_2$C$_{18}$[a] | CO$_2$C$_{18}$ | OH | H | H | >95,2S | |
| b | b | OH | H | H | 10,2R | |
| 1:1 Mixtures | | | | | | |
| CO$_2$Et | CO$_2$Et | OH | H | H | >90,2S | |
| CO$_2$Et | CONH$_2$ | OH | H | H | | |
| CO$_2$Et | CO$_2$Et | OH | H | H | >90,2S | |
| CONH$_2$ | CONH$_2$ | OH | H | H | | |
| CO$_2$Et | CO$_2$Et | OH | H | H | 0 | |

[a] C$_{18}$ = Stearyl b —O, —O (dioxolane-type group with X)

c Mixture of tartrate enantiomers

It is evident from the above table, that while a variety of different chiral carbinols can be used, with certain carbinols no asymmetric induction was observed. In some instances, both shown and not shown, the complex precipitated. This was observed with the acid and certain cyclic imides, not shown. While the tartaric acid derivatives appeared to provide optimal results, numerous variations can be made and asymmetric induction observed.

In the next system, a number of different metals were employed as catalysts. No effort was made to optimize the results with each of the metals and some negative results were observed. The procedure described previously was employed using the alpha-phenylcinnamyl alcohol as the allylic alcohol. The following table indicates the results.

TABLE IV

| Catalyst Precursor(CP)[c] | Chiral Carbinol(CC)[d] | CC/CP mole ratio | Temp °C. | Time hr | Yield % | % ee nmr[a] |
|---|---|---|---|---|---|---|
| Ti(OiPr)$_4$ | (+)DET | 1.11 | 0 | ≦0.5 | 87 | >95 |
| Zr(OiPr)$_4$iPrOH | (+)DET | 1.11 | 0 | ~0.5 | 86 | 10[b] |
| VO(OiPr)$_3$ | (+)DET | 1.17 | 0 | ~0.2 | 100 | 17[b] |
| Nb(OEt)$_5$ | (+)DET | 1.11 | 20 | <24 | ~71 | 0 |
| Ta(OEt)$_5$ | (+)DET | 1.12 | 0 | ~7 | ~90 | ~50[b] |
| MoO$_2$(acac)$_2$ | (+)DiPrT | 2.0 | 20 | 10 days | ~88 | ~15[b] |

[a] As the acetate.
[b] Reverse configurations from the titanium product
[c] iPr - isopropyl
Et - ethyl
acac - acetylacetone
[d] DET - diethyl tartrate
DiPrT - diisopropyl tartrate It is evident from the above results that a number of different metals can provide asymmetric induction. While titanium provides the highest asymmetric induction, vanadium has been found to be faster in its catalytic effect, while also providing some asymmetric induction.

The next aspect to be considered is a general procedure devised for asymmetric epoxidation of homoallylic alcohols.

Into a dry N$_2$ purged flask is added with stirring 10 mmol of homoallylic alcohol, 11 mmol of (+) diethyl tartrate and 30 ml of dry dichloromethane and while maintaining the flask under a positive pressure, the flask is cooled to about −50° C. Titanium isopropoxide (10 mmol) is syringed into the flask and after a 5 minute interval, 20 mmol of an anhydrous solution of t-butylhydroperoxide is syringed in and the mixture stirred for 5-30 min. After removing the flask from the cooling bath, it is put into a refrigerator and maintained at −20° to −18° C. After from about 1-7 days, while monitoring by tlc and glc, when the reaction appears to have terminated, the mixture is worked up by adding about 50 ml of diethyl ether and 10 ml saturated aqueous sodium sulphate and stirring the mixture vigorously for 30-60 min.

The mixture is filtered through a cake of celite, the precipitate washed with diethyl ether, any aqueous phase in the filtrate removed, the organic phase dried and the product isolated.

In addition to the above allylic alcohols, (+)Disparlure, the gypsy moth sex attractant was prepared in accordance with the following synthetic procedure.

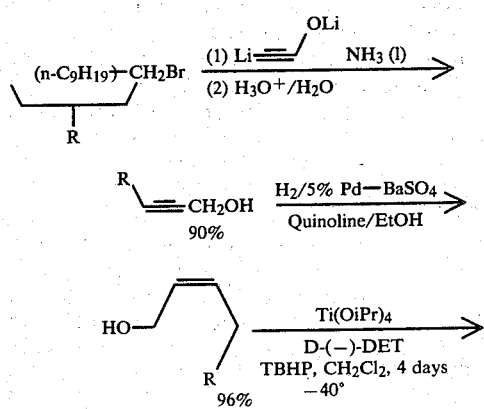

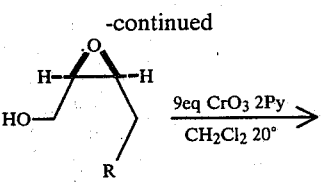

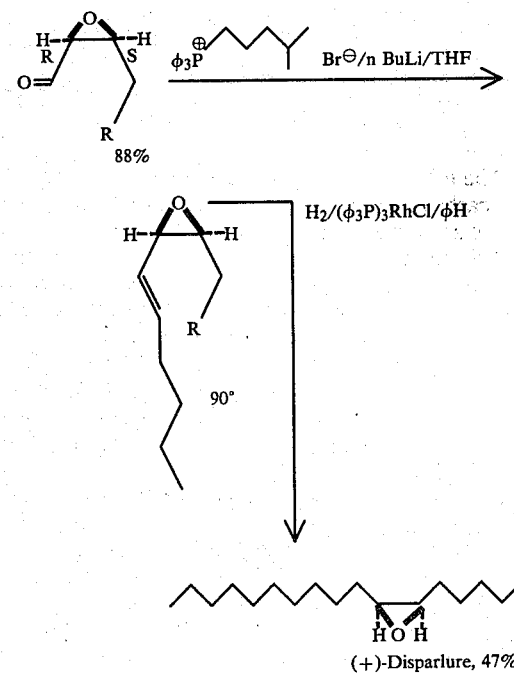

(+)-Disparlure, 47%

The same system which is selective for the maiden introduction of chirality by epoxidation is also very sensitive to pre-existing chirality in an alcohol substrate having a nearby functionality capable of accepting an oxygen atom. Thus, when a racemic carbinol capable of accepting an oxygen atom is exposed to the chiral oxidation system, one of the enantiomers is oxidized much more rapidly than the other.

A reaction was carried out employing a racemic mixture of 3-hydroxy-4 methylpentene-1 with titanium isopropoxide, L-(+)-diethyl tartrate and TBHP in methylene dichloride at 0° C., in accordance with the conditions described above. When epoxidation was carried to 70% completion, the recovered allylic alcohol was greater than >99.99% optically pure. When the reaction was carried to 45% completion, the epoxy alcohol formed was almost pure erythro and was >95% optically pure. The titanium tartrate expoxidation catalyst greatly favors production of erythro epoxyalcohols. It is much more erythro selective than any other known catalyst.

The following examples are illustrative of kinetic resolutions of beta, gamma-unsaturated alcohols. The first resolution is of 3-hydroxy-5-phenylpentene-1.

Into a nitrogen flushed flask fitted with a serum cap was introduced dry dichloromethane (10 ml/mmol of alcohol) and cooled to about −23° C. To the solvent is added sequentially by syringe 1 eq. titanium tetraisopropoxide, 1.2 eq. L-(+)-diisopropyl tartrate and after stirring for 5 min, 1 eq. of the alcohol, followed by 0.7 eq. of anhydrous t-butylhydroperoxide (ca. 4–6M in $CH_2Cl_2$). The resulting homogeneous solution was then stored 12 days at −20° C. in a sealed vessel.

The reaction mixture was worked up by pouring it into a 10% aqueous tartaric acid solution (2 ml/mmol of alcohol) while stirring at room temperature and the stirring continuing for one hour. The two layers were clear. The aqueous layer was separated and the organic layer washed with water and concentrated to a yellow oil.

The oil was diluted with diethyl ether (2 ml/mmol of alcohol) and the resulting solution cooled in an ice bath, 10% aqueous sodium hydroxide added (2 ml/mmol of alcohol) and the mixture stirred at 0° for one hour. The ether phase was washed with water and concentrated to give a yellow oil. The oil was combined at room temperature with isopropylamine (0.5 ml/mmol of alcohol) and water (0.1 ml/mmol of alcohol). After stirring for three days at room temperature, the mixture was concentrated in vacuo, ether added (2 ml/mmol of alcohol) and the organic layer washed first with water and then with 20% hydrochloric acid. After drying ($MgSO_4$), the organic layer was concentrated and distilled. The optically pure product distilled at 90° C. (0.2 mmHg) and gave a 38% yield (76% based on available enantiomer). $[\alpha]^{23}_D$ −1.28 [c14.1, ethanol]. The aqueous phase was stirred with 10% sodium hydroxide (10 min., 0.1 ml/mmol of alcohol) and extracted with ether. The ether solution was washed with water, dried over $MgSO_4$, concentrated in vacuo and the crude product recrystallized from an ether-petroleum ether mixture, yielding a solid product m.p. 72° C. The product was N-isopropyl 2R,3S-dihydroxy-5-phenylpentylamine-1. $[\alpha]^{23}_D$ −22.7 [c2.55, ethanol].

The next resolution involved a propargyl alcohol, namely 3-hydroxyundecine-4. Into the reaction flask was introduced 1 eq. of titanium tetraisopropoxide, 1.2 eg of L-(+)-diisopropyl tartrate, 1 eq. of the alcohol and dry dichloromethane (10 ml/mmol of alcohol) at room temperature. To the mixture with stirring was added 4 eq. of anhydrous t-butylhydroperoxide (ca 4–6M in dichloromethane) and the homogeneous mixture maintained at room temperature for 7 days, while the course of the reaction was followed by GC to 53% conversion. The reaction mixture was then poured into about two volumes (based on volume of reaction mixture) of acetone containing water (ml of $H_2O$ equal to ml of titanium isopropoxide). After stirring at room temperature, the mixture was filtered, concentrated and chromatographed providing the 3R-acetylene compound in 82% yield (based on available enantiomer). $[\alpha]^{24}_D$ +2.68 [c4.43, ethanol]. The product was correlated with the ethylenic analog by reduction using the Lindler catalyst indicating 21% ee.

The next resolution was of ipsdienol which involved combining a mixture of L-(+)-diisopropyl tartrate (2.93 g, 12.5 mmol), titanium isopropoxide (3 ml, 10 mmol) and 100 ml of dry dichloromethane under nitrogen at 0° with stirring for 15 min. Commercial dl-ipsdienol (1.68 g, 10 mmol) and 0.6 ml of n-pentadecane (as glc internal standard) in 20 ml of dichloromethane were added, the mixture cooled to −45° C. and 1.2 ml of anhydrous t-butylhydroperoxide (ca 6.54M in dichloromethane) was added by syringe and the mixture stirred at −45° C. for 21 hours.

The mixture was then poured into 120 ml of acetone containing 10 ml of water, and the resulting mixture stirred at room temperature for 1.5 hour. After filtration and concentration, glc analysis indicated 60% of the starting alcohol was consumed. The residue was taken up in 80 ml of diethyl ether and stirred with 30 ml of 1N sodium hydroxide at 0° C. for 0.5 hr to hydrolyse and remove the tartrate. The ether layer was separated, the aqueous layer was extracted with 20 ml of ether and the combined organic solutions washed once with 30 ml of brine and dried over sodium sulfate. After concentration, the crude residue is purified on basic aluminum oxide (Baker, pH8) eluted with 5% acetone/ether to yield 0.6 g of the resolved alcohol as a clear oil. $[\alpha]^{23}_D$ −12.0 [c1.64, ethanol] e.e. >95%. After further treatment as described above with 0.4 eq. of t-butylhydroperoxide at −50° C. for another 22 hrs., 0.35 g of (−)-R-ipsdienol was obtained with approximately 100% ee.

It is evident from the above results that an extremely potent reaction system is provided for producing optically active compounds, either by introducing an epoxide asymmetrically, or by reacting with one of two enantiomers, so as to provide optically active starting material, as well as optically active product. The reaction is simple, can employ readily available and inexpensive materials, and can be used for a wide variety of applications.

Although the foregoing invention has been described in some detail by way of illustration and example for purposes of clarity of understanding, it will be obvious that certain changes and modifications may be practiced within the scope of the appended claims.

What is claimed is:

1. A method for asymmetrically epoxidizing a carbinol compound having an ethylene group from 0 to 1 carbon atoms from said carbinol;

said method comprising:
   combining in an inert dry medium under mild conditions a metal alkoxide catalyst wherein said metal is titanium or tantalum and has a coordination number of at least 4 and wherein one of said alkoxide groups is optically active; said carbinol compound; and a hydroperoxide;
   wherein said ethylenic bond is asymmetrically oxidized to form an epoxide.

2. A method according to claim 1, wherein said inert medium is halocarbon.

3. A method according to claim 1, wherein said metal alkoxide catalyst includes at least one glycol, wherein each of the carbinol carbon atoms are asymmetric.

4. A method according to claims 1, 2 or 3, wherein said mild conditions include a temperature below about 80° C.

5. A method according to claim 1, wherein said catalyst has as a unit formula: one titanium, two alkoxides, and one tartrate derivative.

6. A method for asymmetrically transferring an oxygen atom to a carbinol compound having a functionality characterized by (1) having a site of ethylenic unsaturation; and (2) said ethylenic unsaturation is separated from said carbinol by from 0 to 1 atoms; said method comprising:

combining in an inert dry medium under mild conditions:

(1) a catalyst comprising as a unit formula one atom of tetravalent titanium, two alkoxide groups and one glycol, wherein the carbinol carbon atoms of said glycol are separated by from 0 to 1 atoms and are asymmetric at each of said carbinol carbon atoms;

(2) said carbinol compound; and
(3) a hydroperoxide, whereby said carbinol compound is asymmetrically oxidized to provide an optically active epoxide.

7. A method according to claim 6, wherein said double bond is allylic.

8. A method according to claim 6, wherein said catalyst is prepared by combining titanium tetraalkoxide and said glycol in an inert medium, and distilling off the alcohol which forms.

9. A method according to claim 6, wherein said glycol is a tartrate other than the acid or its salts.

10. A method according to claim 9, wherein said tartrate is a diester.

11. A method according to claim 10, wherein the ester is a dialkyl ester of alkyl groups of from 1 to 6 carbon atoms.

12. A method according to claim 9, wherein said tartrate is an amide.

* * * * *